US008968687B2

(12) United States Patent
Han et al.

(10) Patent No.: US 8,968,687 B2
(45) Date of Patent: *Mar. 3, 2015

(54) METHOD FOR RECYCLING METALS

(71) Applicant: Industrial Technology Research Institute, Hsinchu (TW)

(72) Inventors: Yin-Lung Han, Tainan (TW); Tai-Rong Guo, Zhubei (TW); Jo-Shu Chang, Taichung (TW); Yung-Chong Lou, Tainan (TW); Wan-Ju Yu, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/143,268

(22) Filed: Dec. 30, 2013

(65) Prior Publication Data

US 2014/0193316 A1 Jul. 10, 2014

Related U.S. Application Data

(63) Continuation-in-part of application No. 13/846,224, filed on Mar. 18, 2013, now Pat. No. 8,828,238.

(60) Provisional application No. 61/652,522, filed on May 29, 2012.

(30) Foreign Application Priority Data

Nov. 22, 2012 (TW) ............................. 101143616 A

(51) Int. Cl.
*C22B 3/00* (2006.01)
*C07K 14/00* (2006.01)
*C02F 3/00* (2006.01)
*C12N 1/02* (2006.01)
*C12N 1/20* (2006.01)
*C22B 7/00* (2006.01)
*C07K 14/195* (2006.01)
*C02F 5/08* (2006.01)
*C12R 1/01* (2006.01)
*C12P 3/00* (2006.01)

(52) U.S. Cl.
CPC ............... *C22B 7/006* (2013.01); *C07K 14/195* (2013.01); *C22B 11/04* (2013.01); *C22B 11/042* (2013.01); *C02F 5/08* (2013.01); *C12R 1/01* (2013.01); *C12P 3/00* (2013.01)
USPC ............... 423/1; 530/400; 530/350; 210/601; 435/261; 435/252.1

(58) Field of Classification Search
CPC ............ A61K 35/74; C12R 1/01; C02F 5/08; C12P 7/065; D06M 16/003; C22B 7/006; C22B 11/04; C22B 11/042; C07K 14/195; C23F 11/14
See application file for complete search history.

(56) References Cited

U.S. PATENT DOCUMENTS

| | | |
|---|---|---|
| 4,480,036 A | 10/1984 | Morgan et al. |
| 7,093,663 B1 | 8/2006 | Bader |
| 8,192,854 B2 | 6/2012 | Borole |
| 8,202,716 B2 | 6/2012 | Thompson et al. |

OTHER PUBLICATIONS

Albuquerque et al., Systematic and Applied Microbiology, 29:450-456, 2006.
Khoo et al., "Interactions of calcium and other metal ions with caldolysin, the thermostable proteinase from *Thermus aquaticus* strain T351", Biochem. J. (1984) vol. 221, pp. 407-413.
Chen et al., "*Tepidimonas taiwanensis* sp. nov., a novel alkaline-protease-producing bacterium isolated from a hot spring," Extremophiles, vol. 10, 2006 (Published online: Oct. 8, 2005), pp. 35-40.
U.S. Office Action dated Apr. 24, 2014 for U.S. Appl. No. 13/846,224.
Chen, Wen-Ming et al., "*Tepidimonas fonticaldi* sp. nov., a slightly thermophilic betaproteobacterium isolated from a hot spring." International J. of Systematic and Evolutionary Microbiology, vol. 63, 2013, pp. 1810-1816.
Office Action for Taiwan Application No. 10321713450 issued Dec. 5, 2014.

*Primary Examiner* — Jennifer McDonald
*Assistant Examiner* — Qing Xu
(74) *Attorney, Agent, or Firm* — Birch, Stewart, Kolasch & Birch, LLP

(57) ABSTRACT

A method for recycling metals is provided by using extracellular proteins excreted by a specific thermophilic bacteria strain, *Tepidimonas fonticaldi* sp. nov., in which the extracellular proteins show excellent metal-ion binding ability, being useful in recycling rare earth metal ions and precious metal ions from geothermal fluids, boiler solutions, industrial wastewater or hard water.

8 Claims, 20 Drawing Sheets

SEQUENCE LISTING

<160> NUMBER OF SEQ ID NOS: 3

<210> SEQ ID NO 1
<211> LENGTH: 1276
<212> TYPE: DNA
<213> ORGANISM: Tepidimonas thermarum AA-1

<400> SEQUENCE: 1

```
gggtgctgac gagtggcgaa cgggtgagta atgcatcgga acgtgcccag aggtggggga      60
taacgcagcg aaagctgtgc taataccgca tgtgatctga ggatgaaagc gggggaccaa     120
gcagcaatgt ttggcctcgc gcctctggag cggccgatgt cagattaggt agttggtggg     180
gtaaaggcct accaagccga cgatctgtag ctggtctgag aggacgacca gccacactgg     240
gactgagaca cggcccagac tcctacggga ggcagcagtg gggaattttg gacaatgggc     300
gcaagcctga tccagcaatg ccgcgtgcgg gaagaaggcc ttcgggttgt aaaccgcttt     360
tgtacggaac gaaaaggctc tggctaatac ctggggctga tgacggtacc gtaagaataa     420
gcaccggcta actacgtgcc agcagccgcg gtaatacgta gggtgcgagc gttaatcgga     480
attactgggc gtaaagcgtg cgcaggcggt cttgtaagac agaggtgaaa tccctgggct     540
caacctagga atggcctttg tgactgcaag gctggagtgc ggcagagggg gatagaattc     600
cgcgtgtagc agtgaaatgc gtagatatgc ggaggaacac cgatggcgaa ggcagtcccc     660
tgggcctgca ctgacgctca tgcacgaaag cgtggggagc aaacaggatt agatacctg      720 gtagtccacg ccctaaacga tgtcgactgg ttgttgggcc ttaggtggct cagtaacgaa     780
gctaacgcgt gaagtcgacc gcctggggag tacggccgca aggttgaaac tcaaaggaat     840
tgacggggac ccgcacaagc ggtggatgat gtggtttaat tcgatgcaac gcgaaaaacc     900
ttacctaccc ttgacatgcc aggaatcctg cagagatgtg ggagtgctcg caagagagcc     960
tggacacagg tgctgcatgg ctgtcgtcag ctcgtgtcgt gagatgttgg gttaagtccc    1020
gcaacgagcg caacccttgc cattagttgc tacgaaaggg cactctaatg ggactgccgg    1080
tgacaaaccg gaggaaggtg gggatgacgt caagtcctca tggcccttat gggtagggct    1140
acacacgtca tacaatggcc ggtacagagg gctgccaacc cgcgaggggg agccaatccc    1200
gtaaaaccgg tcgtagtccg gattgcagtc tgcaactcga ctgcatgaag tcggaatcgc    1260
tagtaatcgc ggatca                                                    1276
```

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2

```
agagtttgat cctggctcag                                                  20
```

<210> SEQ ID NO 3
<211> LENGTH: 17
<212> TYPE: DNA
<213> ORGANISM: Artificial Sequence

```
<220> FEATURE:
<223> OTHER INFORMATION: synthetic oligonucleotide

<400> SEQUENCE: 3
aaggaggtga tccagcc                                                17
```

METHOD FOR RECYCLING METALS

CROSS REFERENCE TO RELATED APPLICATIONS

This application is a Continuation-In-Part of pending U.S. patent application Ser. No. 13/846,224, filed Mar. 18, 2013 and entitled "NOVEL THERMOPHILIC BACTERIUM AND USES OF EXTRACELLULAR PROTEINS THEREFROM", which claims the benefit of U.S. Provisional Application No. 61/652,522, filed May 29, 2012. The disclosure of the applications is incorporated herein by reference.

INCORPORATION BY REFERENCE OF SEQUENCE LISTING

A sequence listing submitted as a text file via EFS-Web is incorporated herein by reference. The text file containing the sequence listing is named "0956-A24070-CIP-US_Seq_Listing.txt"; its date of creation is Dec. 20, 2013; and its size is 2,426 bytes.

TECHNICAL FIELD

The technical field relates to applications of extracellular proteins excreted by thermophilic bacteria.

BACKGROUND

Geothermal energy is an abundant green energy from the Earth and has potential for development. However, due to its unique components, a change of temperature or pressure may easily cause geothermal fluids to form scales on the wellbore walls or in the formation fractures, which increases the instability of geothermal fluid production.

An acid or chemical treatment has been internationally used against geothermal scale formation. However, the waste fluids left from the acid or chemical treatment cause severe environmental pollution.

On the other side, precious metals are not rich in industrial wastewater, geothermal fluids or hot springs. Therefore, to extract precious metals from these liquids by using physical or chemical methods is not efficient and the extraction may cause environmental pollution as mentioned above.

Thus, development of green energy with high production efficiency, while being environmentally friendly, is being researched more and more.

SUMMARY

A detailed description is given in the following embodiments with reference to the accompanying drawings.

In one embodiment, the disclosure provides a method for recycling metals, which comprises providing a liquid containing metal ions, contacting the liquid with an extracellular protein(s) excreted by an isolated thermophilic bacteria strain to form a complex of the metal ion and the protein, and collecting the complex. The isolated thermophilic bacteria strain is *Tepidimonas fonticaldi* sp. nov., internationally deposited in the Korean Collection of Type Culture (KCTC) with the deposit number of KCTC 12528BP.

BRIEF DESCRIPTION OF THE DRAWINGS

The present embodiment can be more fully understood by reading the subsequent detailed description and examples with references made to the accompanying drawings, wherein:

Figure 6:
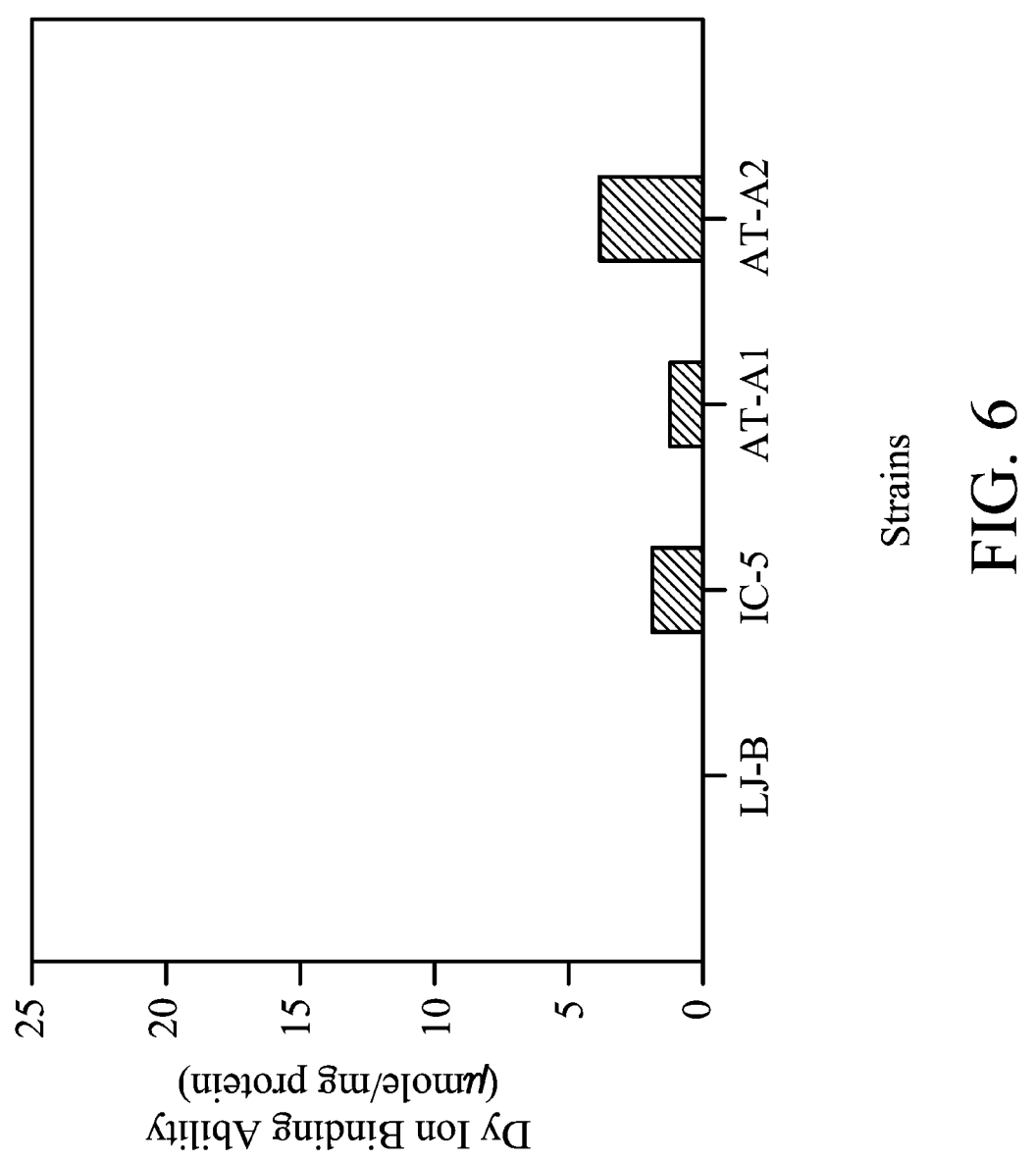

FIG. 6 is a bar graph showing the dysprosium (Dy) ion binding ability of extracellular proteins excreted by various thermophilic strains;

Figure 9:
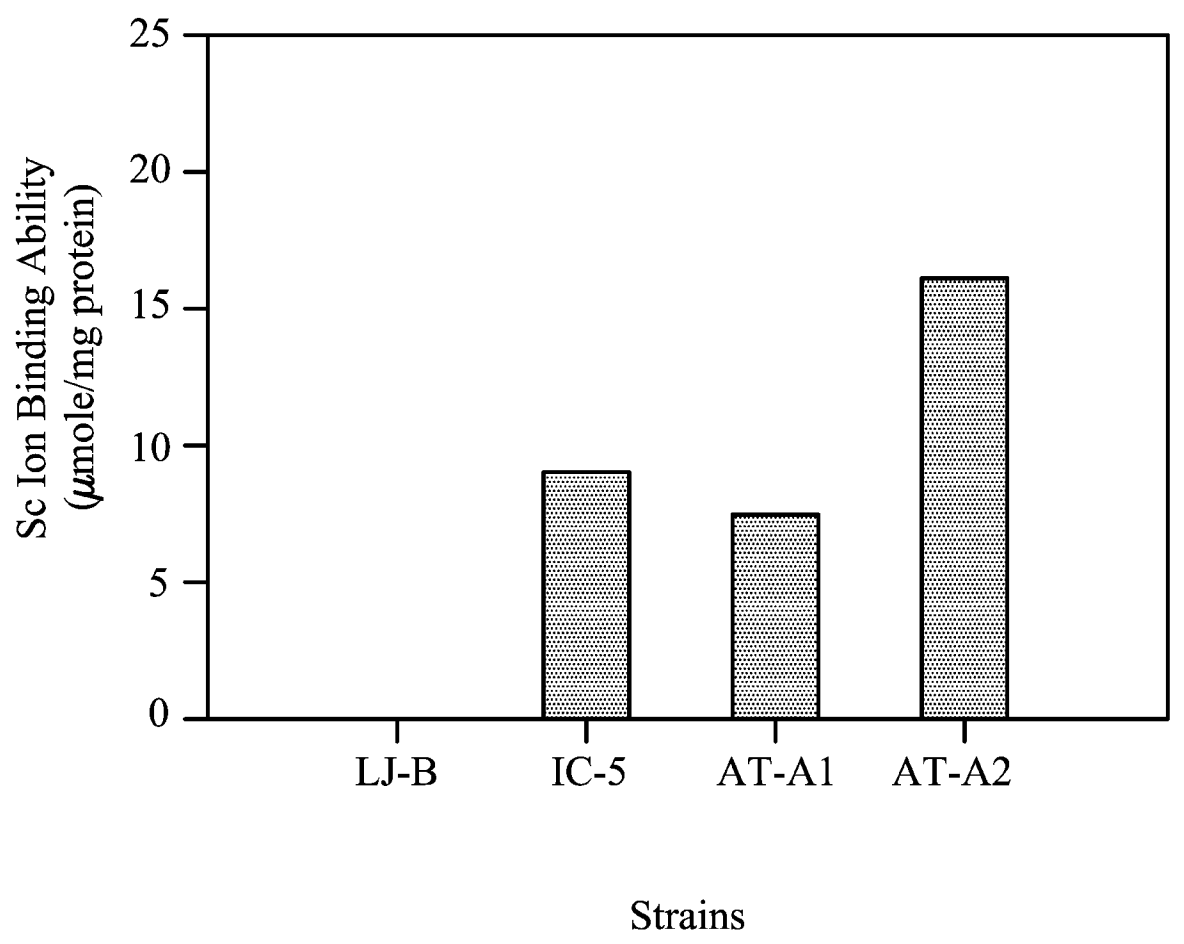

FIG. 9 is a bar graph showing the scandium (Sc) ion binding ability of extracellular proteins excreted by various thermophilic strains;

DETAILED DESCRIPTION

Figure 1:
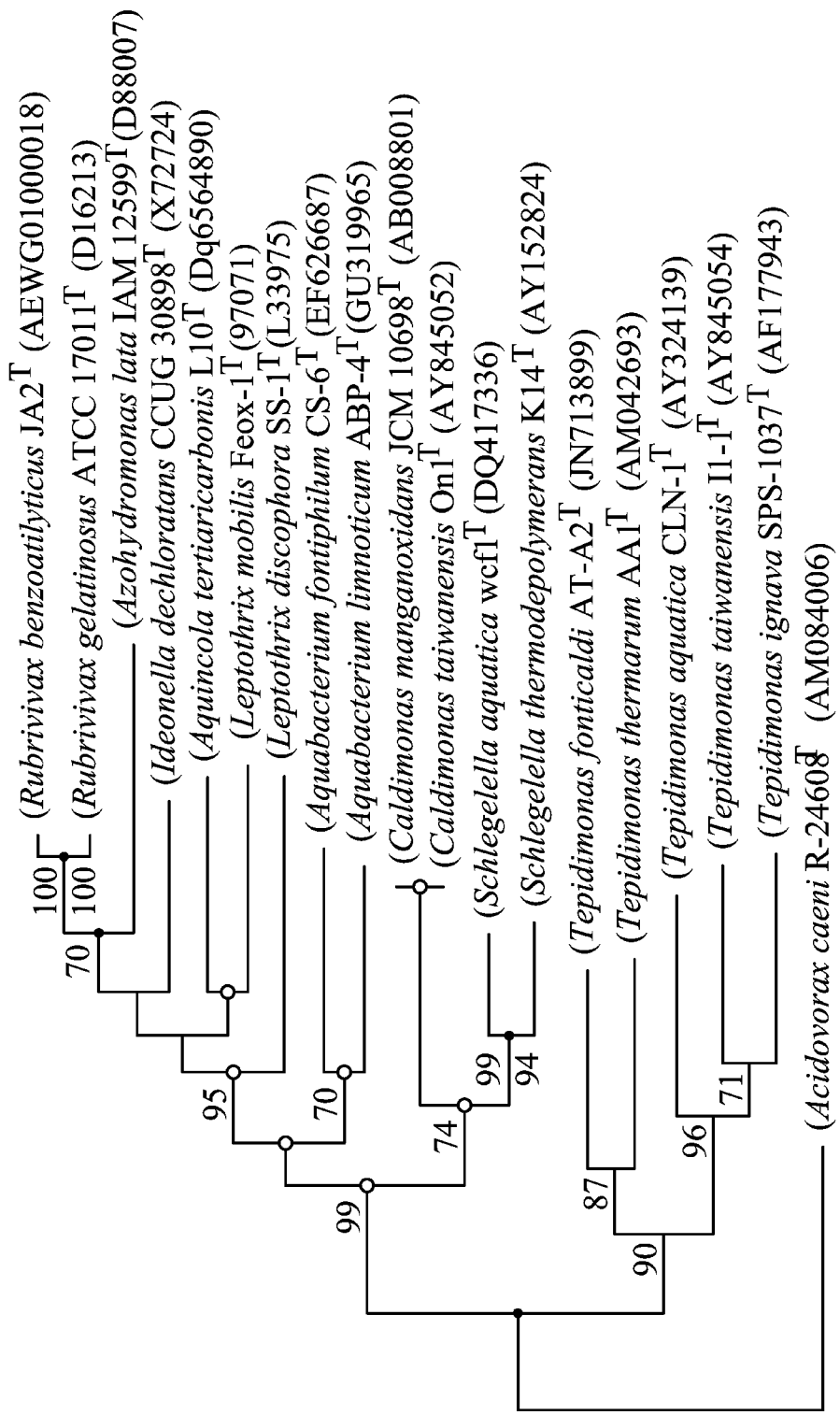
FIG. 1 shows a phylogenic tree diagram of *Tepidimonas fonticaldi* sp. nov. (AT-A2$^T$), based on the similarity of 16S rDNA, in which "*Tepidimonas fonticaldi* AT-A2$^T$ (JN713899)" represents the strain, *Tepidimonas fonticaldi* sp. nov., disclosed in the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment, the present disclosure uses a thermophilic bacteria strain isolated and purified from hot spring water at the Antun, Hualien County, Taiwan. The isolated thermophilic bacteria strain, after being analyzed and sequenced, shows a sequence of the 16S ribosomal DNA (rDNA) as set forth in SEQ ID No. 1. According to the sequence of the 16S rDNA, the isolated strain (AT-A2$^T$) shows phylogenetically close to the well-known strains, *Tepidimonas thermarum* AA-1$^T$ (97.5% sequence similarity), *Tepidimonas aquatica* CLN-1$^T$ (96.8% sequence similarity), *Tepidimonas ignava* SPS-1037$^T$ (96.4% similarity) and *Tepidimonas taiwanensis* I1-1$^T$ (95.8% sequence similarity). A phylogenetic tree diagram based on the sequence similarity of 16S rDNA is depicted in FIG. 1.

The 16S rDNA sequences of the isolated thermophilic strain (AT-A2$^T$) and *Tepidimonas thermarum* AA-1$^T$ were made to hybridize. A DNA-DNA relatedness was shown as 23.9±0.2%, indicating that the isolated thermophilic strain (AT-A2$^T$) belonged to *Tepidimonas* sp.

On the biological characteristics, the isolated thermophilic bacteria strain (AT-A2$^T$) shows aerobic and Gram negative, and forms non-pigmented colonies and mobiles by a single polar flagellum. An optimal growth occurs at 35~60° C., or 55° C., at 0~1.0 wt % of NaCl, or 0.2 wt % of NaCl, and under a pH 7.0~9.0, or pH 7.0. The predominant cellular fatty acids of the isolated thermophilic strain include $C_{16:0}$ (40.2%), summed feature 3 ($C_{16:1}$ ω7c and/or $C_{16:1}$ ω6c; 20.1%) and $C_{17:0}$ cyclo (11.5%). The major polar fatty acids include phosphatidylethanolamine (PE) and phosphatidylglycerole (PG). The GC content of the total DNA in one cell of the bacterium is 70.1 mol %.

On the basis of the phylogenetic and phenotypic data, the isolated strain is classified as a novel species and named as *Tepidimonas fonticaldi* sp. nov., internationally deposited in the Korean Collection of Type Culture (KCTC) on Dec. 4, 2013 with the deposit number of KCTC 12528BP.

The extracellular protein excreted by *Tepidimonas fonticaldi* sp. nov. shows excellent binding ability to metal ions under appropriate conditions. The metal ion comprises rare earth ions or precious metal ions. The rare earth ion may comprise cerium (Ce), dysprosium (Dy), erbium (Er), europium (Eu), gadolinium (Gd), holmium (Ho), lanthanum (La), lutetium (Lu), neodymium (Nd), praseodymium (Pr), scandium (Sc), samarium (Sm), terbium (Tb), thorium (Th), thulium (Tm), uranium (U), ytterbium (Yb), yttrium (Y), or combination thereof. The precious metal ion may comprise gold (Au), silver (Ag), platinum (Pt), palladium (Pd), rhodium (Rh), iridium (Ir) or combination thereof.

In addition, the extracellular protein excreted by *Tepidimonas fonticaldi* sp. nov. shows excellent binding ability to metal ions, such as bi- or tri-valent metal ions, under appropriate conditions. The bi- or tri-valent metal ions may comprise aluminium (Al), boron (B), barium (Ba), bismuth (Bi), calcium (Ca), cadmium (Cd), cobalt (Co), chromium (Cr), copper (Cu), iron (Fe), gallium (Ga), indium (In), potassium (K), lithium (Li), magnesium (Mg), manganese (Mn), sodium (Na), nickel (Ni), lead (Pb), strontium (Sr), thallium (Tl), zinc (Zn) or combination thereof, but are not limited thereto.

According to the present disclosure, the metal-ion binding ability of the extracellular protein excreted by *Tepidimonas fonticaldi* sp. nov. is not affected by high temperatures, high pressure and/or extreme pH conditions. Specifically, in one example, the extracellular proteins show excellent metal ion binding ability under 100☐, pH 7. In another example, the extracellular proteins show excellent metal ion binding ability under a temperature of 75~150° C., preferably 125~150° C., at 1 atm, pH 7. In another example, the extracellular proteins show excellent metal ion binding ability at a pressure of 1~50 atm, preferably 30~50 atm, at 25° C., pH 7. In another example, the extracellular proteins show excellent metal ion binding ability at acidic condition, like pH 2~6 or basic condition, like pH 7~10, at 25° C., 1 atm.

According to the present disclosure, the method for recycling metals further comprises a step of adding a desorption agent to the complex. The desorption agent causes the metal ion being desorbed from the complex consisted of the extracellular protein and the metal ion. In one example, the desorption agent may comprise nitrilotriacetic acid (NTA), ethylenediaminetetraacetate (EDTA), or combination thereof. In another example, the desorption agent may comprise sulfate, nitrate, hydrochloric acid or combination thereof.

Due to the excellent metal ion binding ability, the extracellular protein according to the present disclosure is able to bind metal ions in the liquid, such as geothermal waters, boiler solutions, industrial wastewater or hard water, in particular, in order to absorb metal ions for recycling the metals. Therefore, the method according to the present disclosure can reduce the pollution of the liquid, like industrial wastewater, and increase the concentration of the metal ions in the wastewater so as to reduce the cost of recycling the metals from the liquid, resulting in an efficient metal recycling.

Example 1

Collection and Identification of *Tepidimonas Fonticaldi* sp. nov.

Collection

10 L of the hot spring water at the Antun, Hualien County, Taiwan was collected with an aluminum foil-wrapped bottle. The collected hot spring water was filtered through a 0.45 μm filter membrane under a sterile condition. The filter membrane was then put onto a 1.5% agarose medium (a mixture of 300 mL of hot spring water and 4.5 g of agarose, under 121° C., heated for 15 minutes and added into a medium plate for cooling) and cultured at 55° C. for 7~14 days. After being cultured, colonies with various colors or shapes were picked up with a sterile inoculating loop and lined on a fresh agarose medium. The steps above were repeated to obtain a pure strain. The isolated strain was stored at 4° C.

Bacteria DNA Extraction

The isolated strain was picked up from the medium with a sterile inoculating loop and added into 1 mL of sterile water. After three times of being washed with sterile water, the genomic DNA of the isolated strain was extracted by using a genomic DNA extraction minoprep system (Blood & Tissue). The extracted genomic DNA was then stored at −20° C.

16S rDNA Sequencing

The extracted genomic DNA underwent a polymerase chain reaction (PCR) following the conditions set forth in Tables 1 and 2 with a universal prokaryotic 16S ribosome PCR primer pair of FD1 (SEQ ID NO. 2) and RD1 (SEQ ID NO. 3) for amplifying the 16S rDNA sequence of the isolated strain. The amplified 16S rDNA was sequenced by Mission Biotech Incorporation, Taiwan.

TABLE 1

PCR Reagents

| Reagents | Volume (µl) |
|---|---|
| DNA templates | 1 |
| Tag buffer (10X) | 2.5 |
| Tag polymerase (2.5 U/µl) | 0.125 |
| dNTP (2.5 mM) | 2 |
| Forward primer (100 pmol/µl) | 1 |
| Reverse primer (100 pmol/µl) | 1 |
| deionized water | 17.5 |
| Total volume | 25 |

TABLE 2

PCR Conditions

| | Temperature and time | Reaction | Cycle numbers |
|---|---|---|---|
| Stage 1 | 95° C. 5 min | Denature | 1 |
| Stage 2 | 95° C. 1 min | Denature | 35 |
| | 56° C. 1 min | Annealing | |
| | 72° C. 1 min | Extending | |
| Stage 3 | 72° C. 4 min | Extending | 1 |

Alignment of 16S rDNA Sequence

The 16S rDNA sequence of the isolated strain was aligned with the GenBank library by using BLAST software (www.ncbi.nlm.nih.gov) and similarities with the published sequences in the library were analyzed. The 16S DNA sequence of the isolated strain was recorded in the NCBI (www.ncbi.nlm.nih.gov) with a series number of JN 713899, named *Tepidimonas fonticaldi* sp. nov.

Construction of the Phylogenic Tree

According to the sequence similarity obtained above, a phylogenic tree diagram was depicted with accession numbers of each strain by using BioEdit software and CLUSTAL_X and homology among these strains was calculated as well. The phylogenic tree diagram is shown in FIG. 1, in which the isolated strain was identified as *Tepidimonas fonticaldi* sp. nov. (AT-A2$^T$)

Example 2

Metal Ion Binding Ability of Extracellular Proteins

Protein Collection

The isolated strain, *Tepidimonas fonticaldi* sp. nov., and a modal strain, *Thermus aquaticus* BCRC 17110, were respectively inoculated in a 100 mL 1/10 TSB medium (1.7 g/L pancreatic digest of casein, 0.3 g/L enzymatic digest of soybean meal, 0.25 g/L dextrose, 0.5 g/L NaCl and 0.25 g/L dipotassium phosphate) and cultured at 200 rpm, at 55° C. for 3~5 days.

The cultured medium was centrifuged at 10,000 rpm for 10 minutes. The supernatant was collected and concentrated by 10 times with a protein concentration system. The concentrated protein was taken as the extracellular proteins for the next steps. Meanwhile, the precipitate of the centrifuged medium was ultrasound vibrated to break the bacteria and the solution was taken as the intracellular proteins for the next steps.

Protein Quantification

The extracellular proteins solution obtained above 100 µL were added with a Bio-Rad protein test reagent 400 µL for a color reaction, occurring within 15 minutes. The absorbance at a wavelength of 595 nm was detected and the protein concentration was calculated.

$Ca^{2+}$ Binding Ability of Extra- and Intra-cellular Proteins

The experiment was designed for investigating the $Ca^{2+}$ binding ability of the extra- and intra-cellular proteins. The extra- and intra-cellular proteins from the thermophilic bacteria listed in Table 3 were all detected for the $Ca^{2+}$ binding ability.

50 ppm of the extra- and intra-cellular proteins obtained from the thermophilic bacteria listed in Table 3 were respectively mixed with the 100 ppm calcium ion solution prepared by $CaCl_2 \cdot 2H_2O$ in a ratio of 1:1. The mixture was heated in 100° C. of a water bath for 1 hour. The mixture was then filtered through an ultrafiltration system with a 3 KDa membrane to capture the proteins. The filtrate was then diluted with deionized water to reach the detection limit (0~5 ppm). The $Ca^{2+}$ concentration left in the filtrate was analyzed by an inductively coupled plasma atomic emission spectrometer (ICP-AES) for calculating the $Ca^{2+}$ binding ability. The results are shown in Table 3 and FIG. 2.

TABLE 3

$Ca^{2+}$ Binding Ability of Extra- and Intra-Cellular Proteins

| | | $Ca^{2+}$ binding ability (mg $Ca^{2+}$/mg protein) | |
|---|---|---|---|
| Strain codes | Strains | Intracellular protein | Extracellular protein |
| IC-5 | 98.764% of 16S DNA similarity with *Anoxybacillus kamchatkensis* JW/VK-KG4$^T$ | 0.012 | 0.034 |
| LJ-B | 98.949% of 16S DNA similarity with *Anoxybacillus mongoliensis* T4$^T$ | 0.005 | 0.069 |
| AT-A1 | 100.00% of 16S DNA similarity with *Meiothermus ruber* DSM 1279$^T$ | 0.006 | 0.032 |
| AT-A2 | *Tepidimonas fonticaldi* sp. nov. | 0.011 | 0.327 |
| BCRC 17110 | *Thermus aquaticus* BCRC 17110 | 0.005 | 0.082 |

Figure 2:
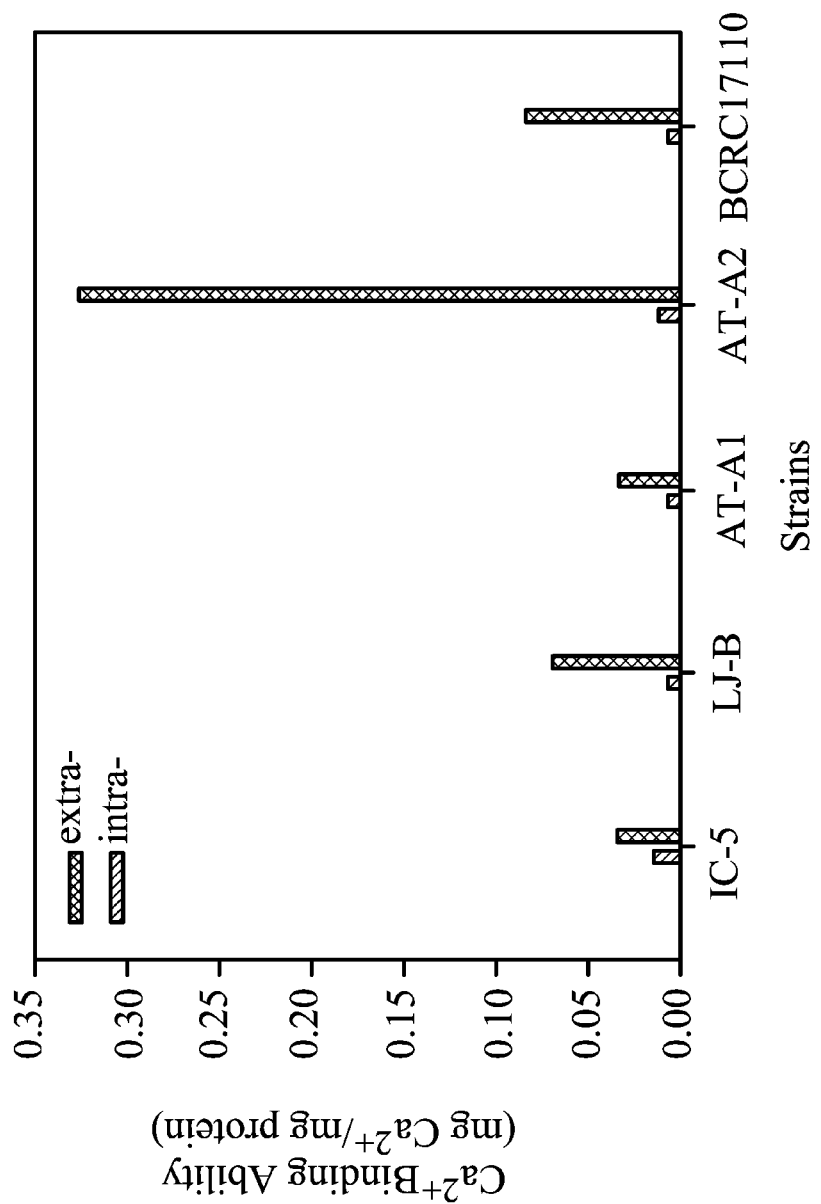
FIG. 2 is a bar graph showing the $Ca^{2+}$ binding ability of intra- and extra-cellular proteins excreted by various thermophilic strains.

As shown in Table 3 and FIG. 2, the $Ca^{2+}$ binding ability of the extracellular proteins was much more significant than that of the intracellular proteins. Meanwhile, the extracellular proteins of the thermophilic bacteria strain, *Tepidimonas fonticaldi* sp. nov. (AT-A2$^T$), showed 0.327 mg of $Ca^{2+}$/mg protein, the best binding ability among these strains. Regarding the other strains, the extracellular proteins merely showed $Ca^{2+}$ binding ability of less than 0.1 mg of $Ca^{2+}$/mg protein.

$Ca^{2+}$ Binding Ability Under Various Conditions

An experiment was designed for investigating the effects of environmental factors, like temperature, pressure, pH value etc., on the $Ca^{2+}$ binding ability of the extracellular proteins from some of the thermophilic bacteria strains listed in Table 3.

The experiment included the three following groups:

Group 1: The extracellular proteins 50 ppm were treated respectively under a pressure of 10 atm, 30 atm and 50 atm, at 25° C., pH 7 for 10 minutes;

Group 2: The extracellular proteins 50 ppm were treated respectively under a pH 2, pH 4, pH 6, pH 7, pH 8 and pH 10 at 25° C., 1 atm for 10 minutes; and Group 3: The extracellular proteins 50 ppm were treated respectively under a temperature of 100° C., 125° C., and 150° C., at 1 atm, pH 7 for 10 minutes.

The treated proteins 50 ppm were separately mixed with a 100 ppm calcium ion solution prepared by $CaCl_2 \cdot 2H_2O$ in a ratio of 1:1. The mixture was heated in a 100° C. water bath for 10 minutes. The mixture was then filtered through an ultrafiltration system with a 3 KDa membrane to capture the proteins. The filtrate was then diluted with deionized water to reach the detection limit (0~5 ppm). The $Ca^{2+}$ concentration left in the filtrate was analyzed by an inductively coupled plasma atomic emission spectrometer (ICP-AES) for calculating the $Ca^{2+}$ binding ability. The results are shown in FIGS. 3~5.

Figure 3:
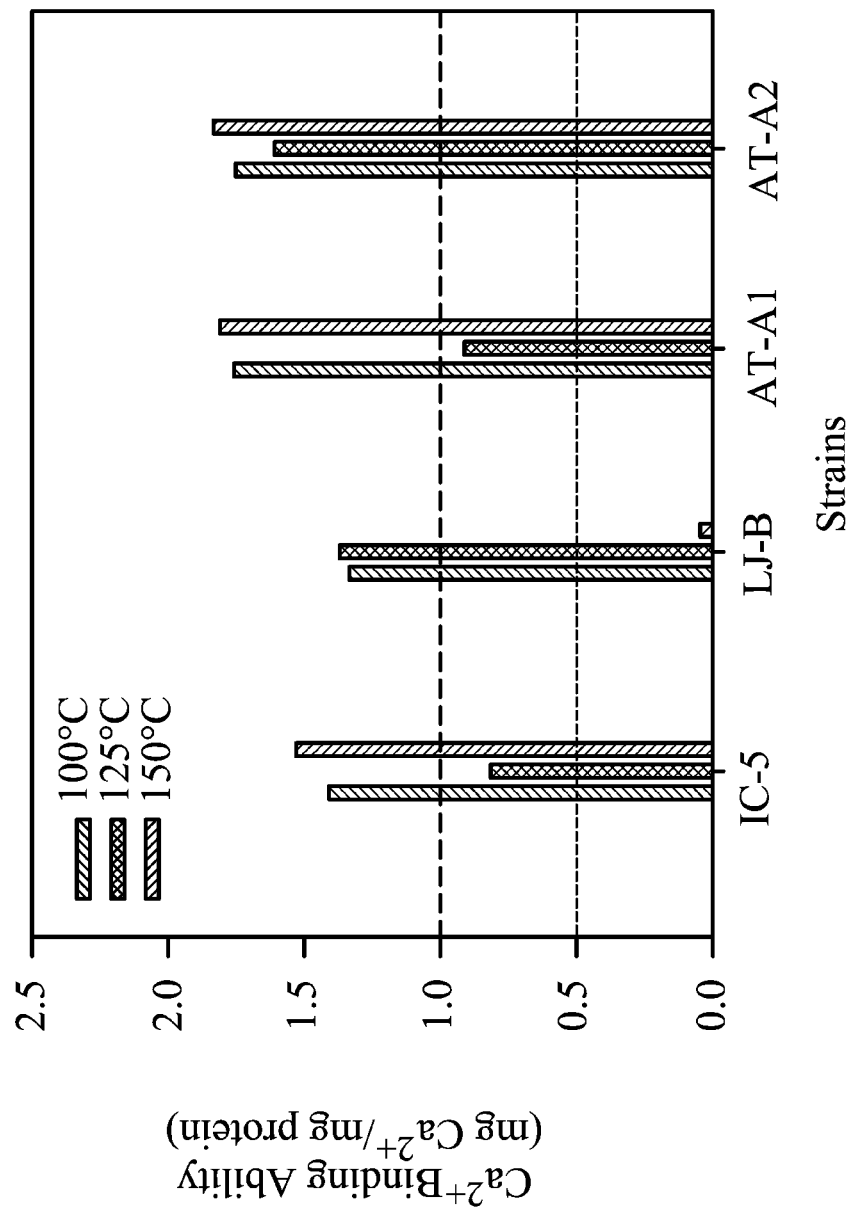
FIG. 3 is a bar graph showing the $Ca^{2+}$ binding ability of extracellular proteins excreted by various thermophilic strains under different temperature conditions.
Figure 4:
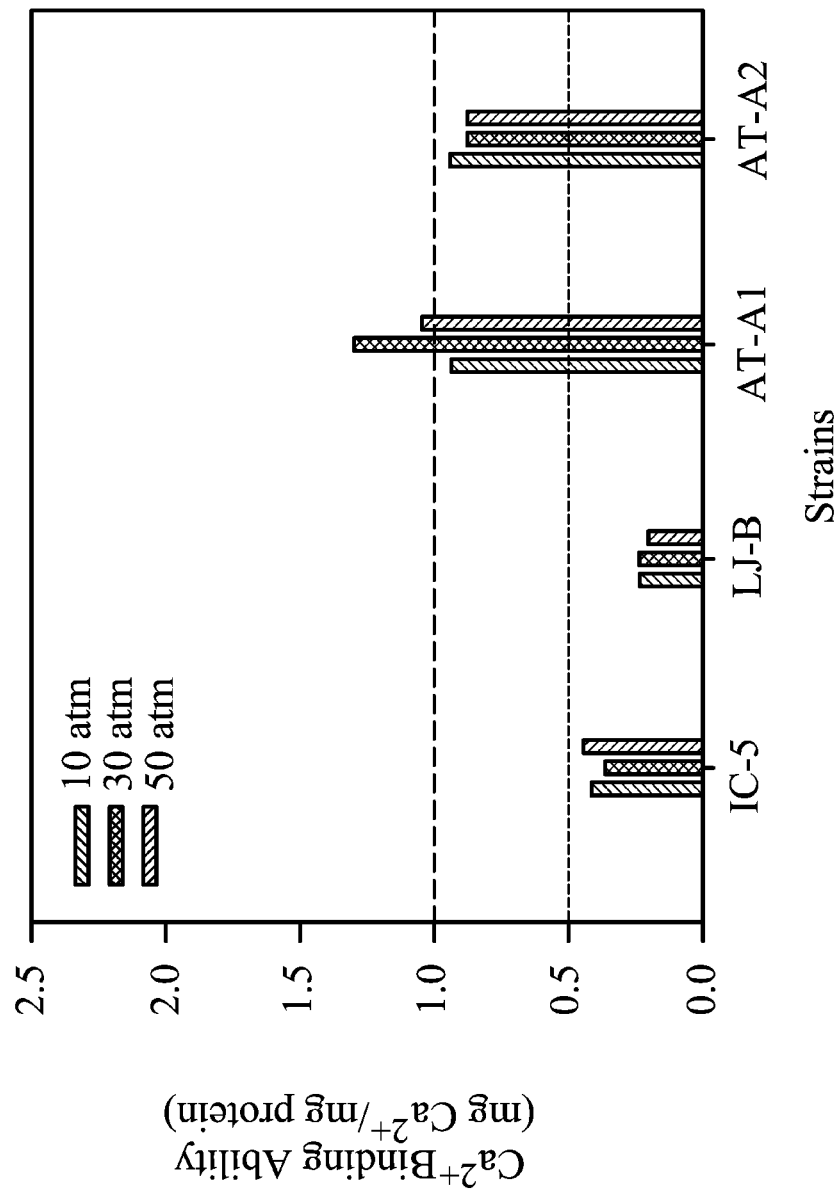
FIG. 4 is a bar graph showing the $Ca^{2+}$ binding ability of extracellular proteins excreted by various thermophilic strains under different pressure conditions.
Figure 5:
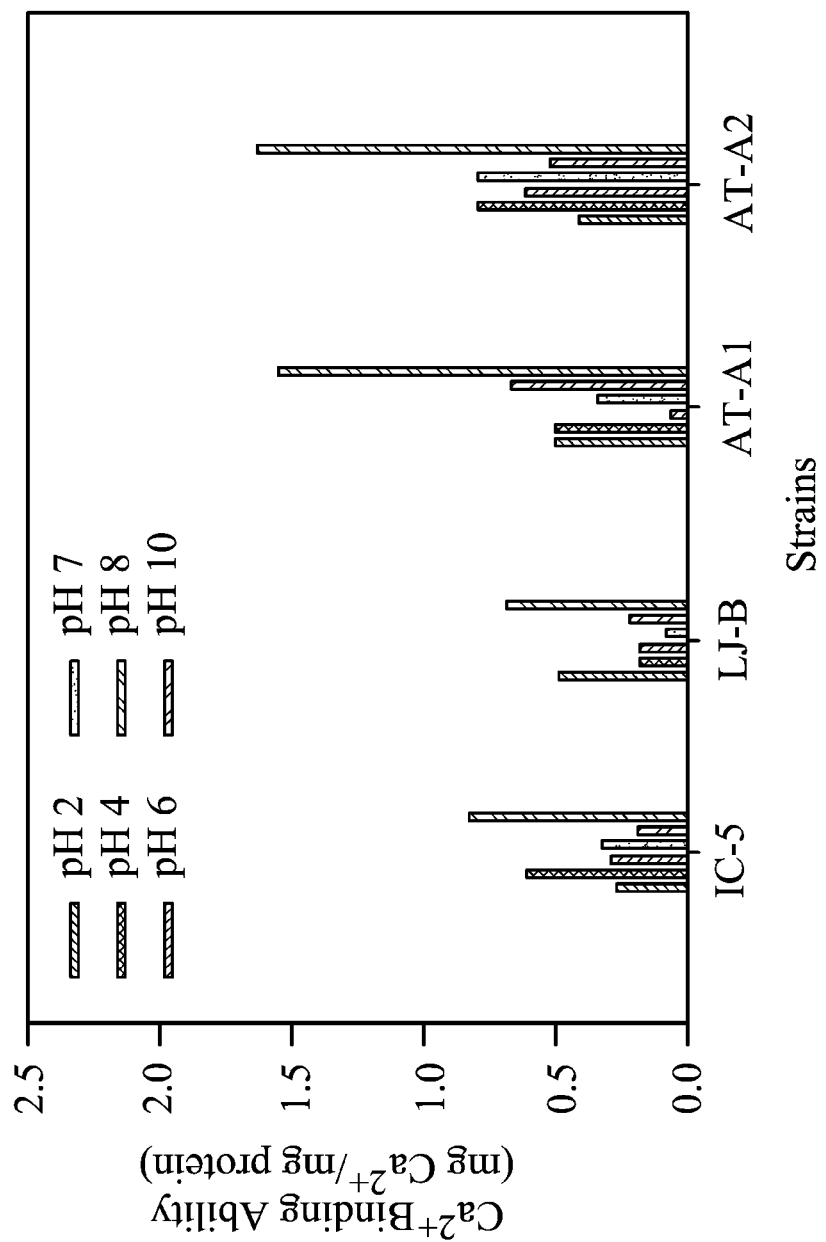
FIG. 5 is a bar graph showing the $Ca^{2+}$ binding ability of extracellular proteins excreted by various thermophilic strains under different pH value conditions.
Figure 7:
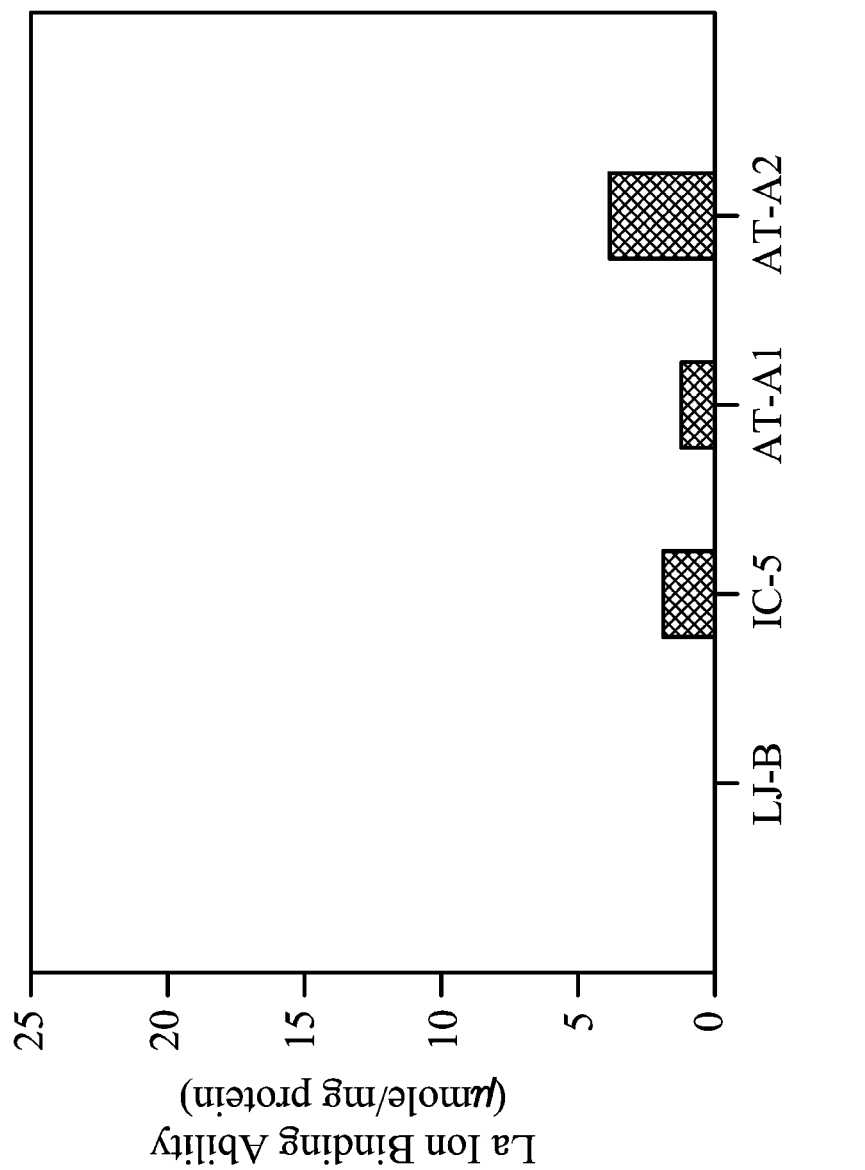
FIG. 7 is a bar graph showing the lanthanum (La) ion binding ability of extracellular proteins excreted by various thermophilic strains.
Figure 8:
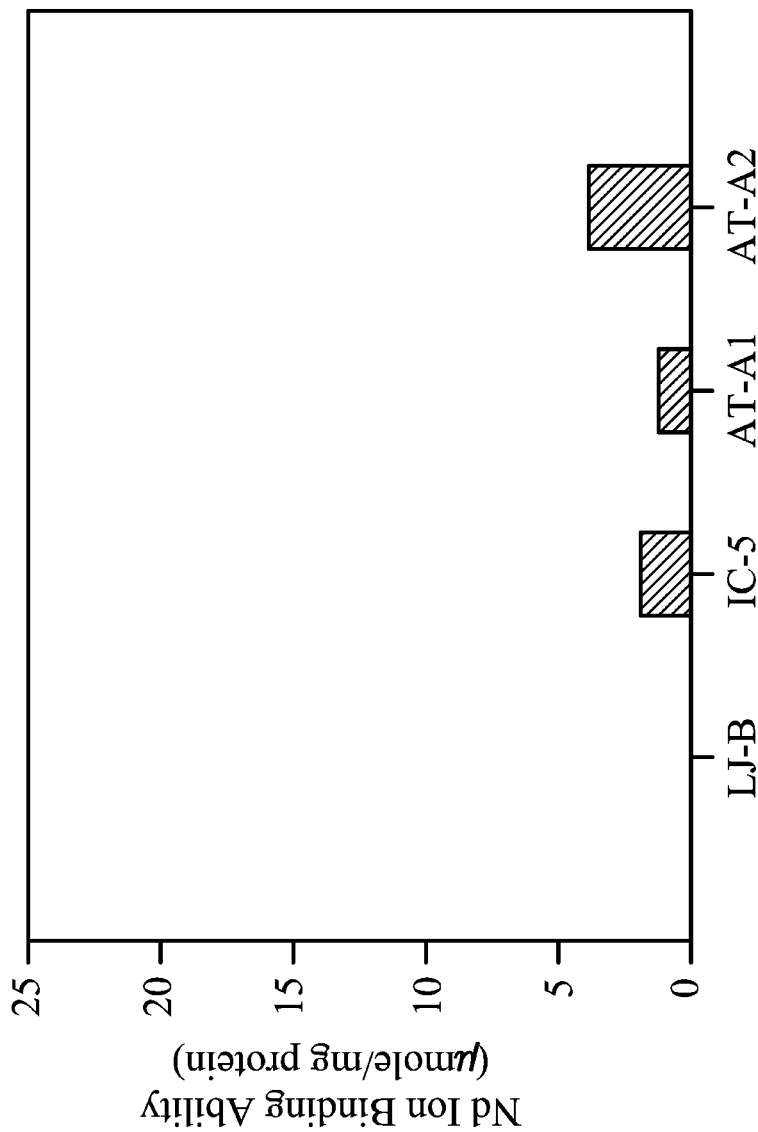
FIG. 8 is a bar graph showing the neodymium (Nd) ion binding ability of extracellular proteins excreted by various thermophilic strains.
Figure 10:
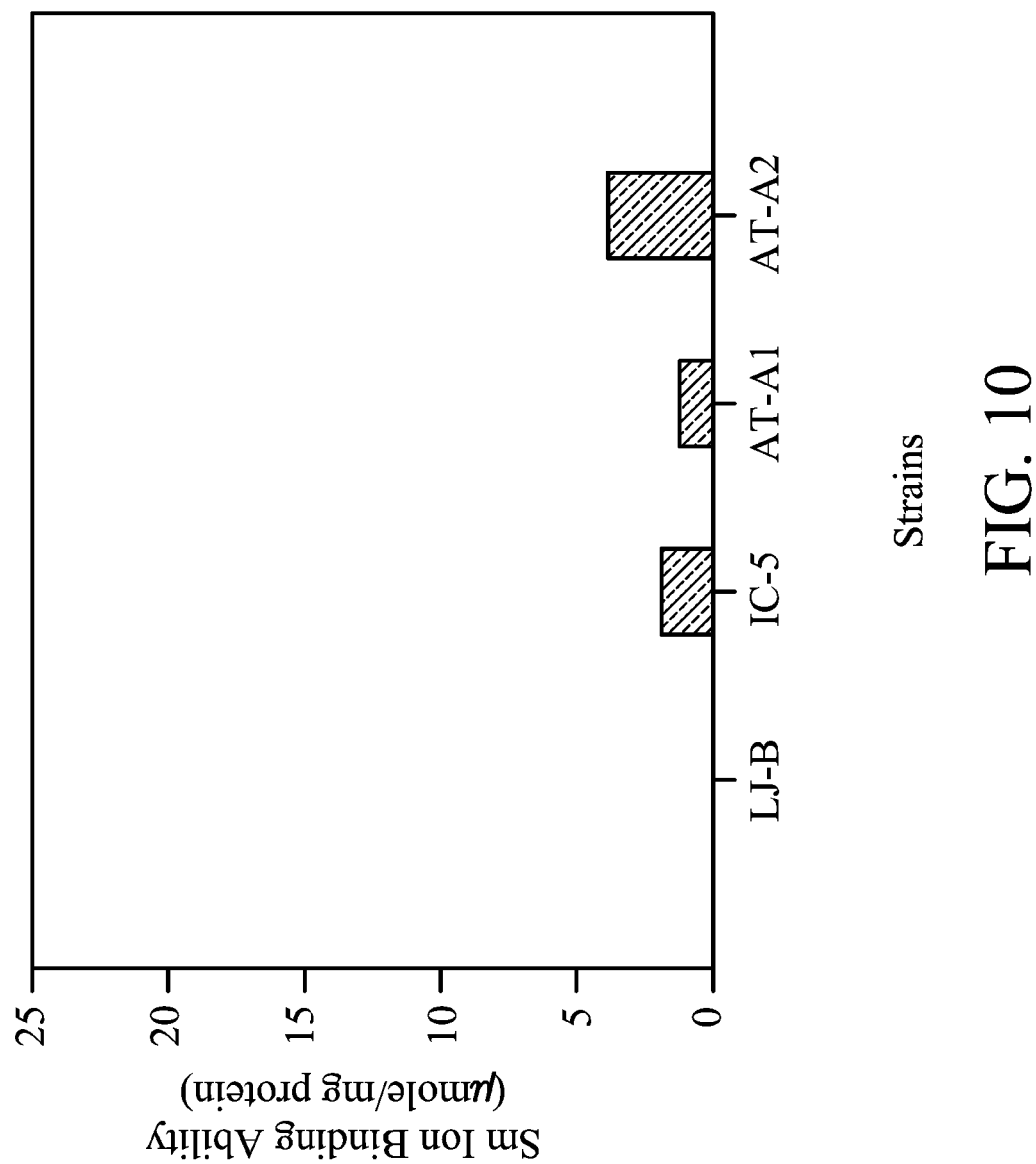
FIG. 10 is a bar graph showing the samarium (Sm) ion binding ability of extracellular proteins excreted by various thermophilic strains.
Figure 11:
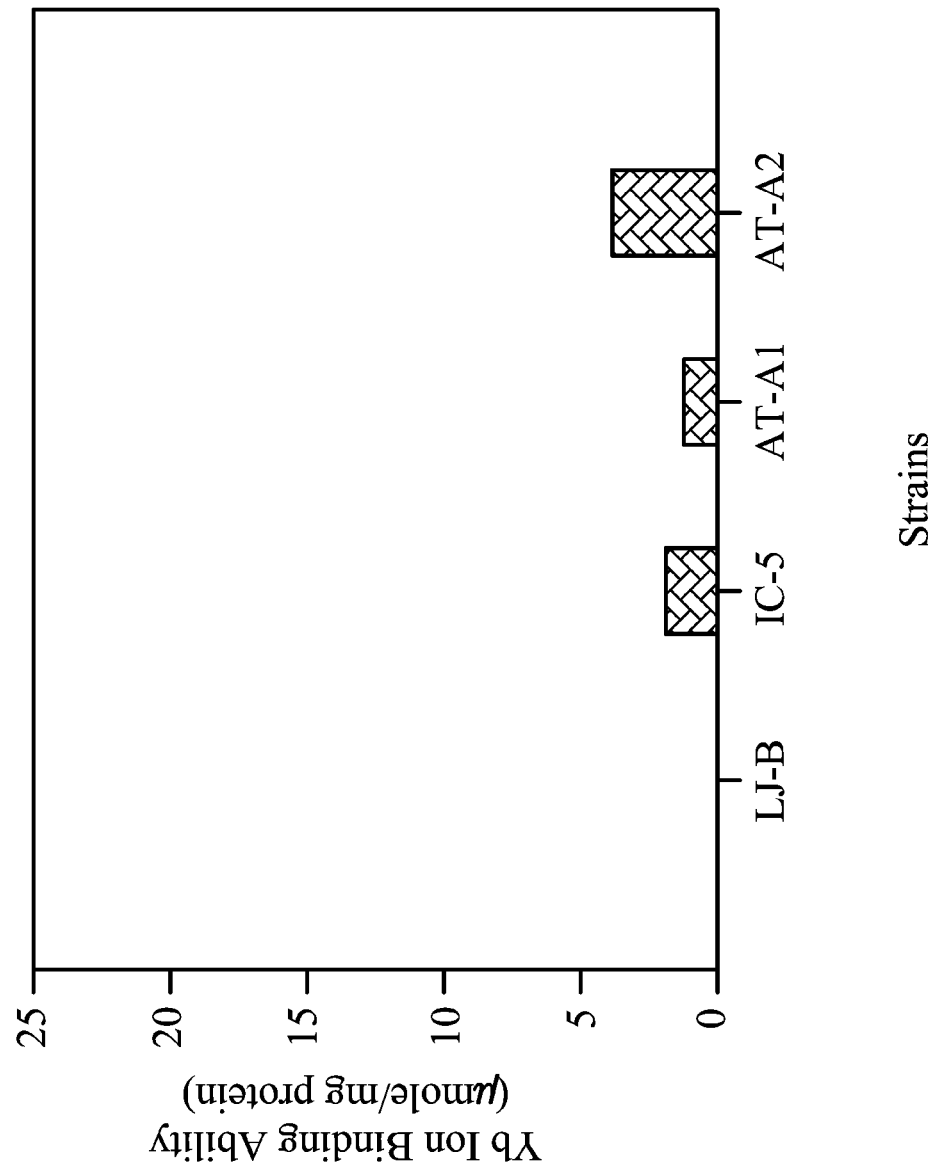
FIG. 11 is a bar graph showing the ytterbium (Yb) ion binding ability of extracellular proteins excreted by various thermophilic strains.
Figure 12:
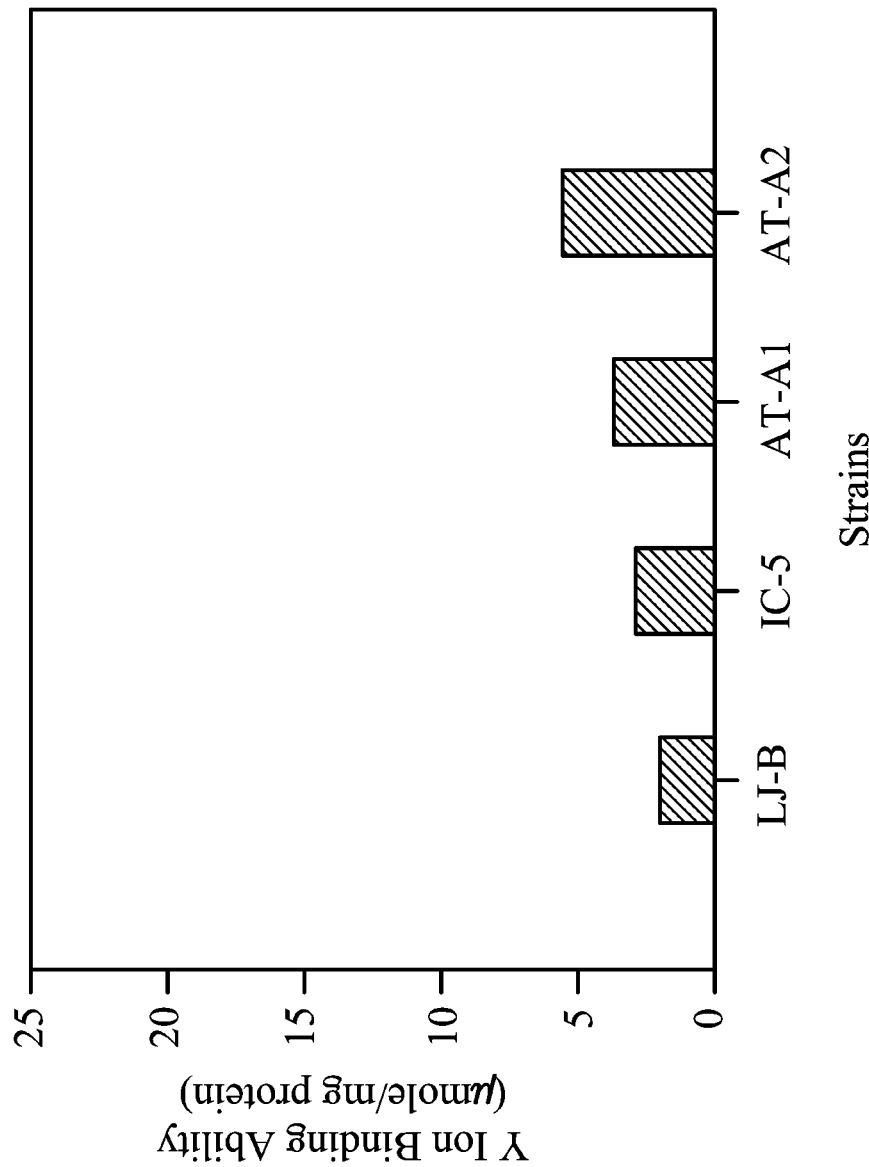
FIG. 12 is a bar graph showing the yttrium (Y) ion binding ability of extracellular proteins excreted by various thermophilic strains.

In FIGS. 3~5, the extracellular proteins from the thermophilic bacteria strain, *Tepidimonas fonticaldi* sp. nov. (AT-A2$^T$), showed excellent $Ca^{2+}$ binding ability under high temperatures, high pressure and broad pH values.

Rare Earth Ion Binding Ability

An experiment was designed for investigating the rare earth ion binding ability of the extracellular proteins excreted by some of the thermophilic bacteria strains listed in Table 3.

The extracellular proteins 10 ppm were mixed with a standard solution 10 ppm in a ratio of 1:1 and reacted at 100° C., pH 2 for 20 minutes. The standard solution included metal ions of cerium (Ce), dysprosium (Dy), erbium (Er), europium (Eu), gadolinium (Gd), holmium (Ho), lanthanum (La), lutetium (Lu), neodymium (Nd), praseodymium (Pr), scandium (Sc), samarium (Sm), terbium (Tb), thorium (Th), thulium (Tm), uranium (U), ytterbium (Yb) and yttrium (Y).

The binding abilities of dysprosium (Dy), lanthanum (La), neodymium (Nd), scandium (Sc), samarium (Sm), ytterbium (Yb) and yttrium (Y) were determined by using the method described above and were shown in a unit of µmole metal ions/mg proteins in FIGS. 6~12, respectively.

Bi- and Tri-Valent Metal Ion Binding Ability

An experiment was designed for investigating the bi- and tri-valent metal ion binding ability of the extracellular proteins from some of the thermophilic bacteria strains listed in Table 3.

Figure 13:
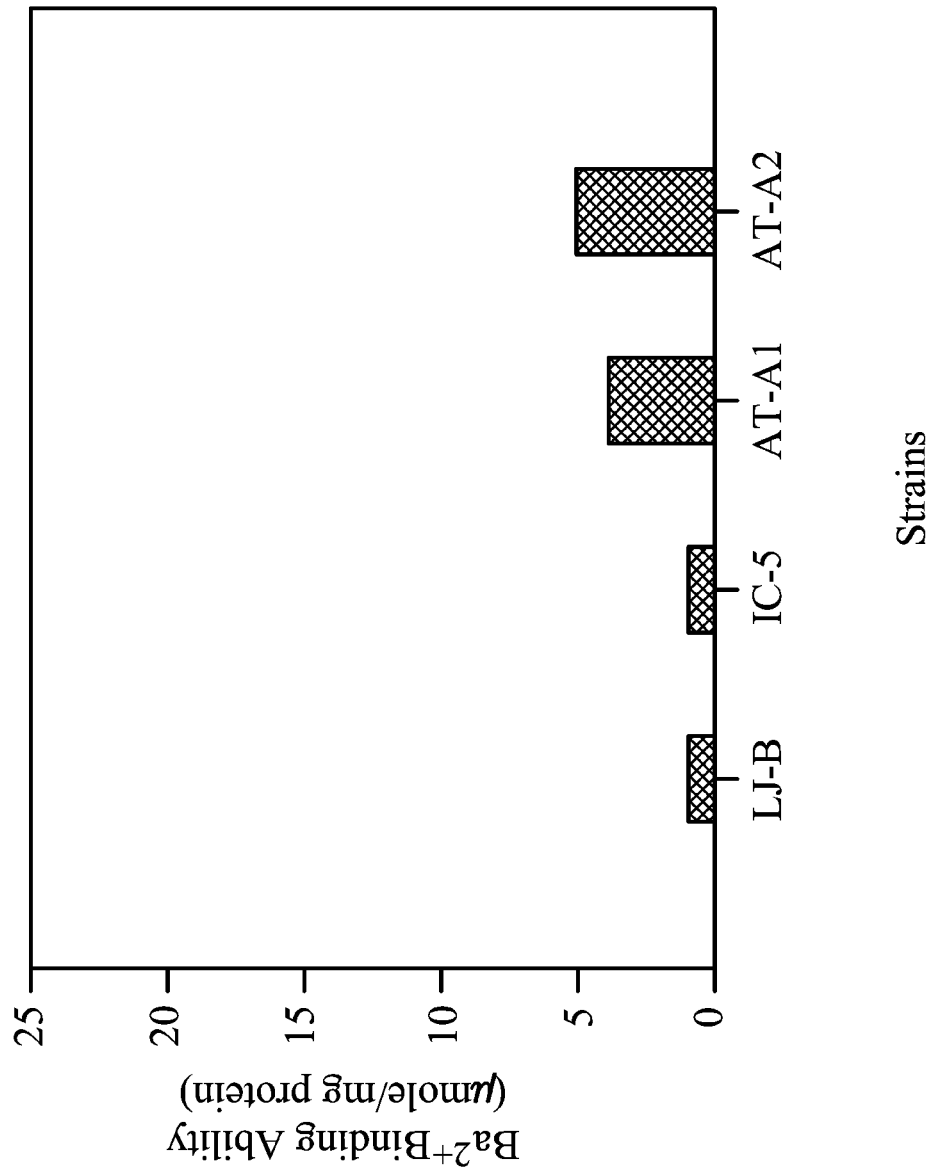
FIG. 13 is a bar graph showing the barium (Ba) ion binding ability of extracellular proteins excreted by various thermophilic strains.
Figure 14:
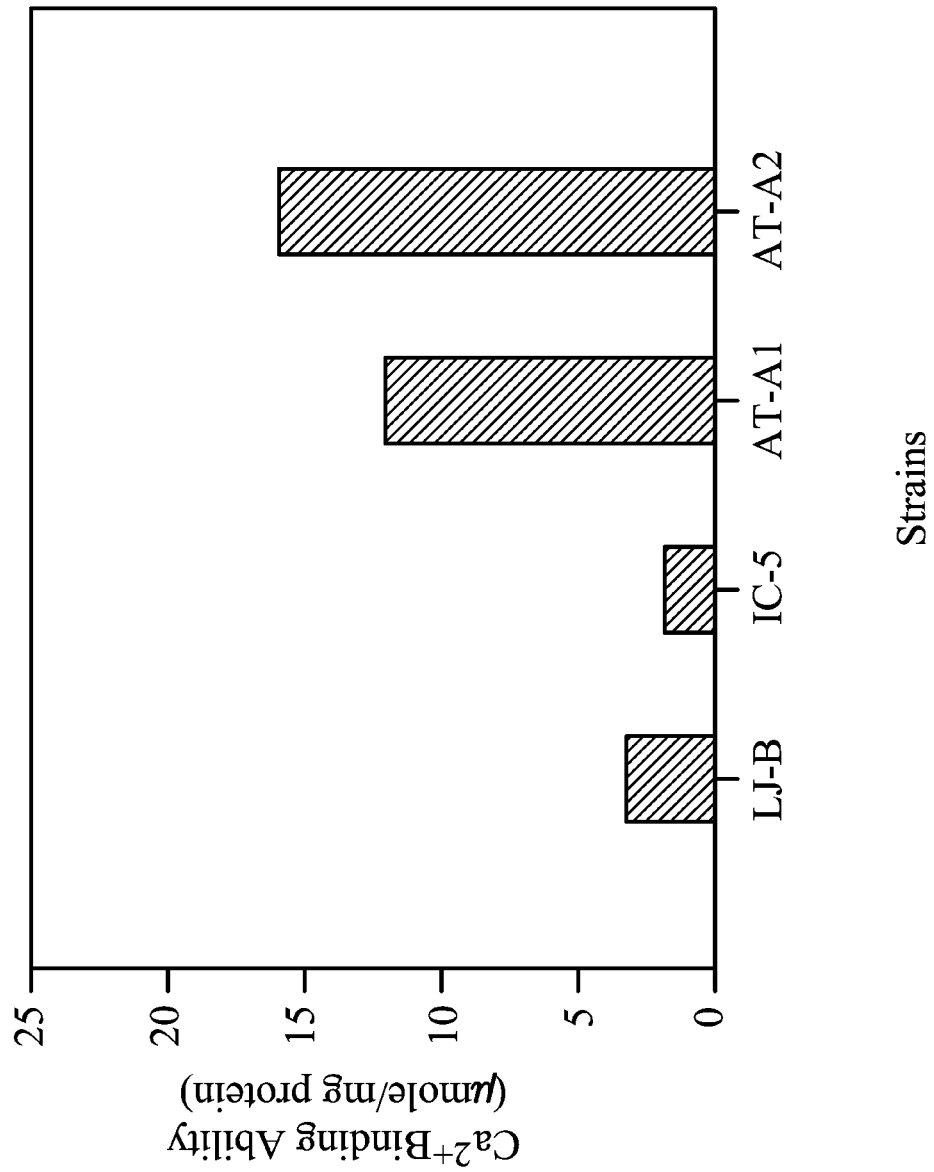
FIG. 14 is a bar graph showing the calcium ion ($Ca^{2+}$) binding ability of extracellular proteins excreted by various thermophilic strains.
Figure 15:
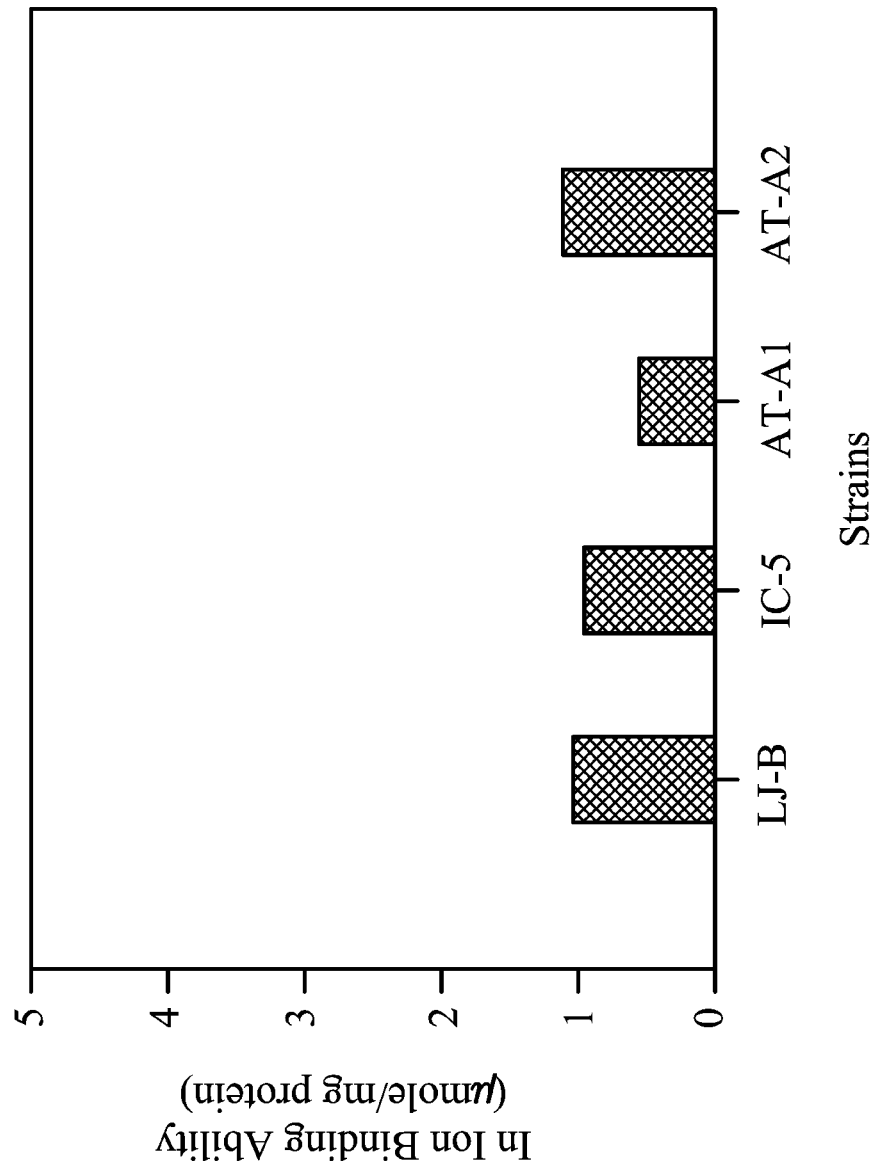
FIG. 15 is a bar graph showing the indium ion (In) binding ability of extracellular proteins excreted by various thermophilic strains.
Figure 16:
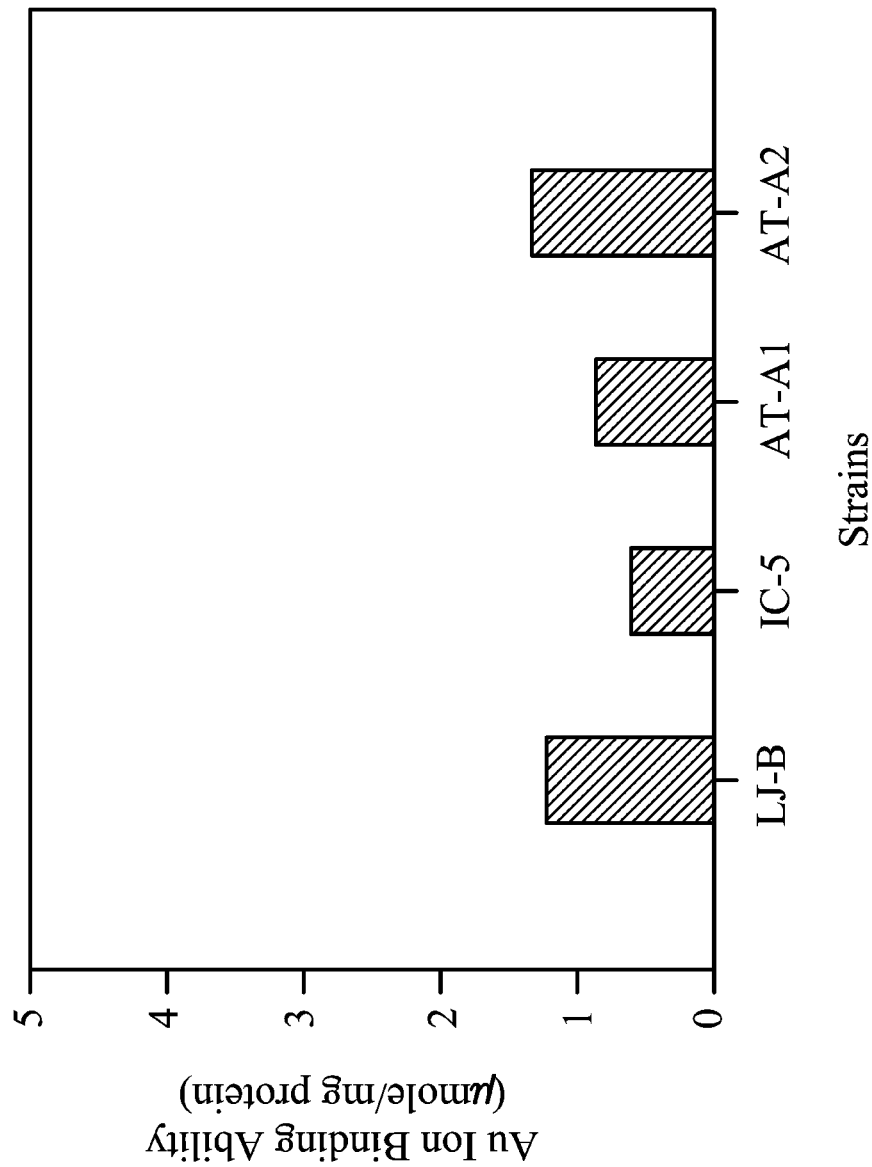
FIG. 16 is a bar graph showing the gold ion (Au) binding ability of extracellular proteins excreted by various thermophilic strains.
Figure 17:
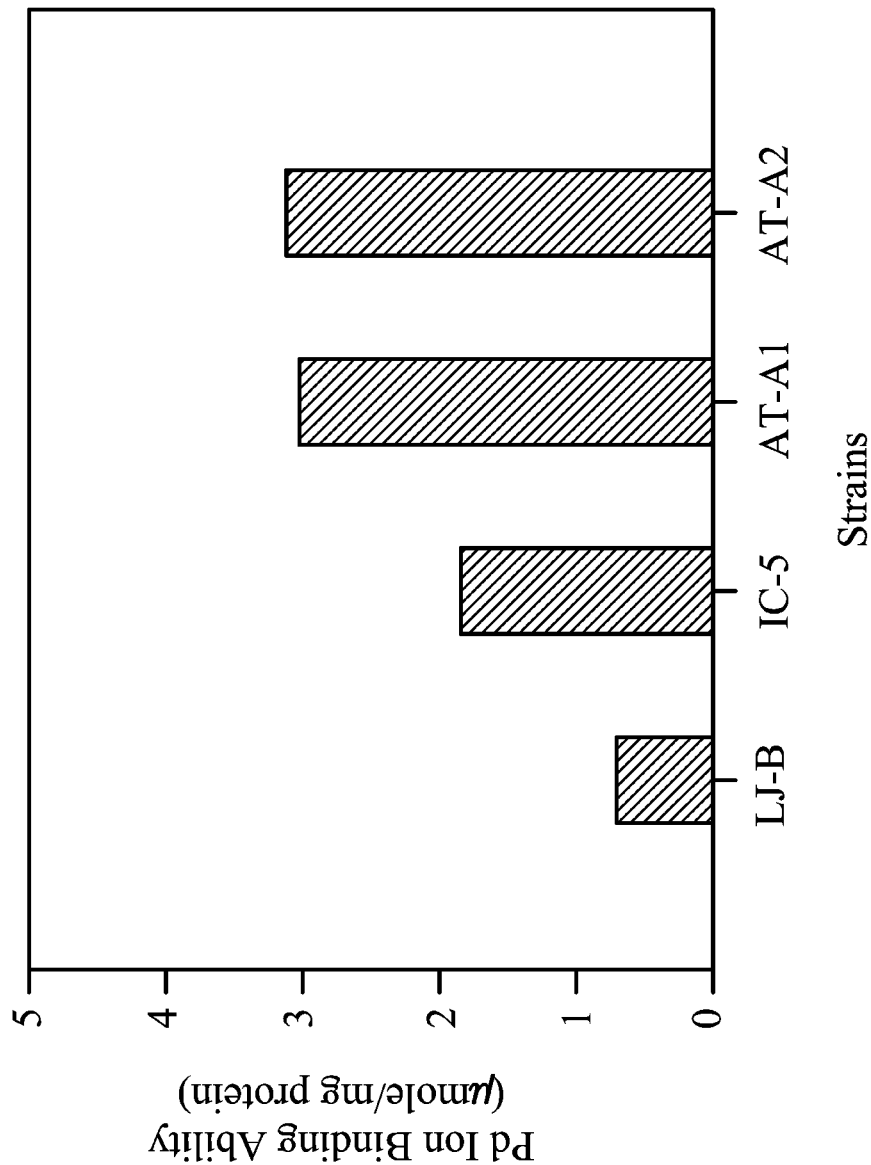
FIG. 17 is a bar graph showing the palladium ion (Pd) binding ability of extracellular proteins excreted by various thermophilic strains.
Figure 18:
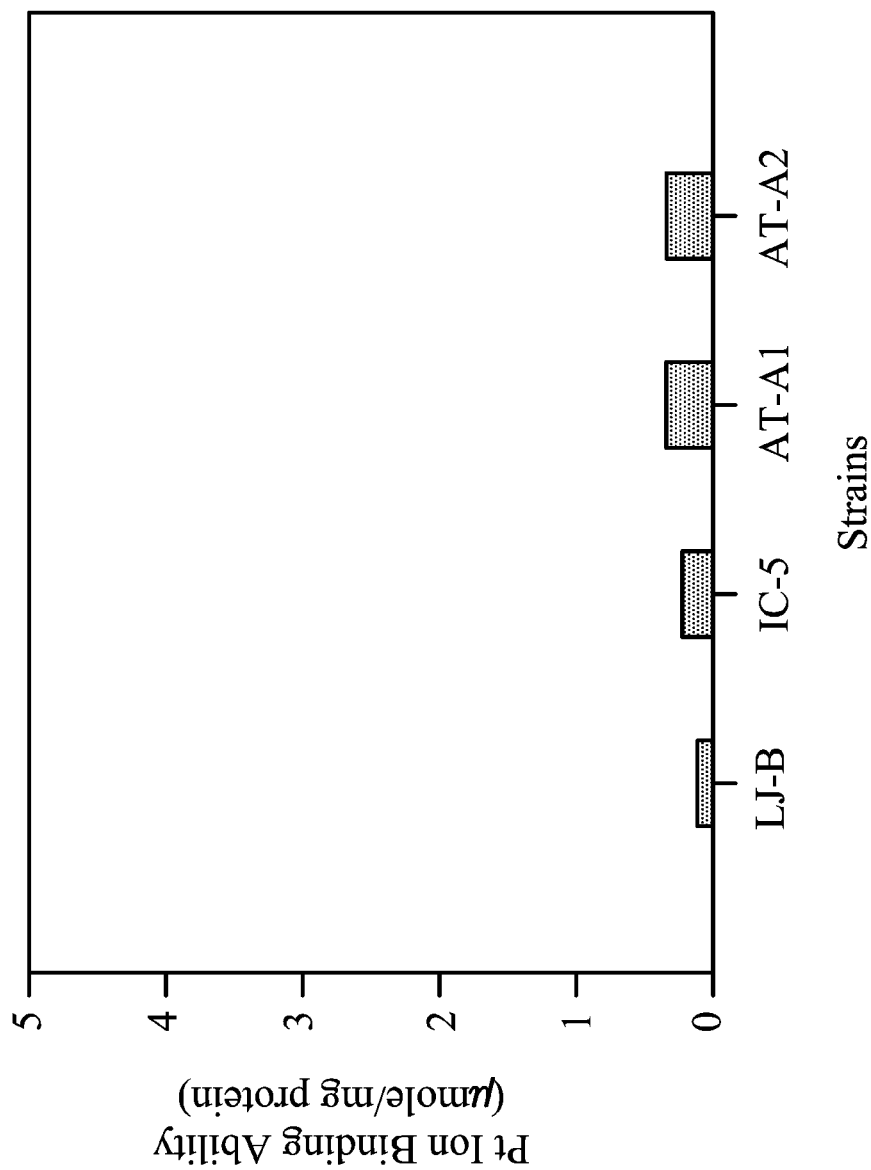
FIG. 18 is a bar graph showing the platinum ion (Pt) binding ability of extracellular proteins excreted by various thermophilic strains.
Figure 19:
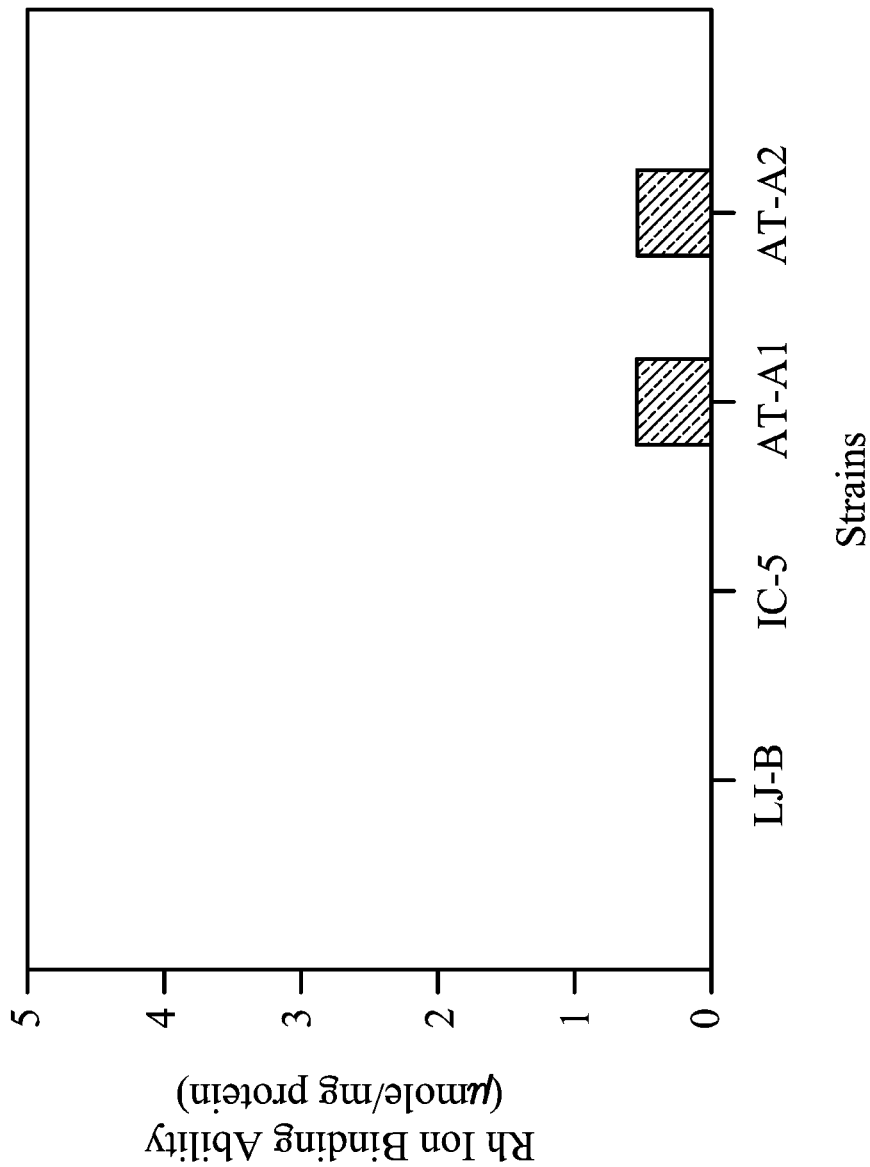
FIG. 19 is a bar graph showing the rhodium ion (Rh) binding ability of extracellular proteins excreted by various thermophilic strains.

The extracellular proteins 10 ppm were mixed with a standard solution 10 ppm in a ratio of 1:1 and reacted at 100° C., pH 2 for 20 minutes. The standard solution included metal ions of aluminium (Al), boron (B), barium (Ba), bismuth (Bi), calcium (Ca), cadmium (Cd), cobalt (Co), chromium (Cr), copper (Cu), iron (Fe), gallium (Ga), indium (In), potassium (K), lithium (Li), magnesium (Mg), manganese (Mn), sodium (Na), nickel (Ni), lead (Pb), strontium (Sr), thallium (Tl) and zinc (Zn). The binding abilities of barium (Ba) ions, calcium (Ca) ions and indium (In) ions were determined by using the method described above and were shown in a unit of µmole metal ions/mg protein in FIGS. 13~15, respectively.

Precious Metal Ion Binding Ability

An experiment was designed for investigating the precious metal ion binding ability of the extracellular proteins excreted by some of the thermophilic bacteria strains listed in Table 3.

The extracellular proteins 10 ppm were mixed with a standard solution 10 ppm in a ratio of 1:1 and reacted at 100° C., pH 2 for 20 minutes. The standard solution included metal ions of gold (Au), palladium (Pd), platinum (Pt) and rhodium (Rh). The binding abilities of these ions were determined by using the method described above and were shown in a unit of µmole metal ions/mg protein in FIGS. 16~19, respectively.

As given in FIGS. 6~19, the extracellular proteins from the thermophilic bacteria strain, *Tepidimonas fonticaldi* sp. nov. (AT-A2$^T$), show excellent binding ability broadly to rare earth ions, bi- and tri- valent metal ions and precious metal ions.

Comparative Example 1

Metal Ion Binding Ability Of Commercially Available Proteins 50 ppm of commercially available proteins including ovalbumin, bovine serum albumin (BSA) and lysozyme were mixed with a palladium (Pd) ion standard solution 10 ppm and reacted at 25° C., pH 4 for 60 minutes.

On the other side, 50 ppm of commercially available proteins including ovalbumin, bovine serum albumin (BSA) and 100 ppm of lysozyme were mixed with a gold (Au) ion standard solution 10 ppm and reacted at 25° C., pH 4 for 60 minutes.

The binding ability of the commercially available proteins was determined by the method described in Example 2 and was shown in a unit of µmole metal ions/mg protein.

Figure 20:
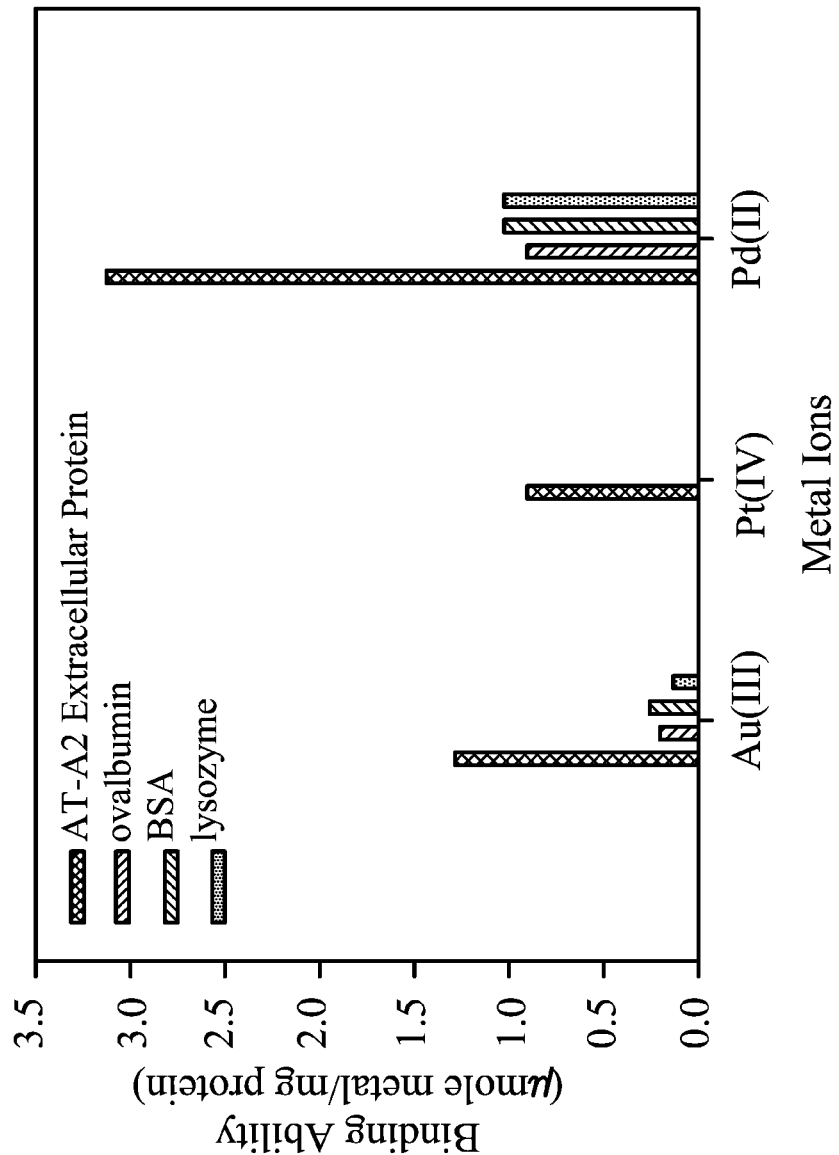
FIG. 20 is a bar graph showing the gold ion (Au) binding ability and the palladium ion (Pd) binding ability of the extracellular protein excreted by *Tepidimonas fonticaldi* sp. nov. (AT-A2 extracellular protein) and commercially available proteins (ovalbumin, BSA and lysozyme).

As given in FIG. 20, the gold (Au) ion binding ability of ovalbumin, bovine serum albumin (BSA) and lysozyme is 0.18, 0.20 and 0.10 µmole metal ions/mg protein, respectively. The palladium (Pd) ion binding ability of ovalbumin, bovine serum albumin (BSA) and lysozyme is 0.86, 0.98 and 0.98µmole metal ions/mg protein, respectively. Meanwhile, the extracellular proteins from the thermophilic bacteria strain, *Tepidimonas fonticaldi* sp. nov. (AT-A2$^T$), show the gold (Au) ion binding ability being 1.33 µmole metal ions/mg protein and the palladium (Pd) ion binding ability being 3.13 µmole metal ions/mg protein in the same figure. These results show that the extracellular proteins from the thermophilic bacteria strain, Tepidimonas fonticaldi sp. nov. (AT-A2$^T$), have better precious metal ion binding ability than the commercially available ones.

Example 3

Desorption of Metal Ions 40 ml of desorption agent, nitrilotriacetic acid, was added into the reaction systems comprising the extracellular proteins and rare earth ions or precious metal ions described in Example 2. The reactants were desorbed at 25° C. for 30 min. The metals in each reaction systems were then collected respectively.

It will be apparent to those skilled in the art that various modifications and variations can be made to the disclosed

What is claimed is:

1. A method for recycling metals, comprising:
   culturing an isolated thermophilic bacterial strain in a culture medium;
   separating the thermophilic bacterial strain from the culture medium, wherein the culture medium comprises a mixture of extracellular proteins excreted by the thermophilic bacterial strain;
   concentrating the culture medium to a concentration of 50 ppm extracellular proteins, thereby obtaining a concentrated culture medium;
   contacting a volume of the concentrated culture medium with an equal volume of a liquid comprising metal ions, thereby forming a complex of the metal ions and the extracellular proteins, wherein the metal ions are from a metal to be recycled;
   collecting the complex of the metal ions and the extracellular proteins;
   adding a desorption agent to the complex of the metal ions and the extracellular proteins;
   wherein the isolated thermophilic bacterial strain is *Tepindimonas fonticaldi* sp. nov., internationally deposited in the Korean Collection of Type Culture (KCTC) with deposit number of KCTC 12528BP, wherein the desorption agent is selected from the group consisting of nitrilotriaceic acid, ethylenediaminetetraacetate, and a combination thereof.

2. The method of claim 1, wherein the metal ions comprise rare earth ions or precious metal ions.

3. The method of claim 2, wherein the rare earth ions comprise cerium (Ce) dysprosium (Dy), erbium (Er) europium (Eu), gadolinium (Gd), holmium (Ho), lanthanum (La), lutetium (Lu), neodymium (Nd), praseodymium (Pr), scandium (Sc), samarium (Sm), terbium (Tb), thorium (Th), thulium (Tm), uranium (U), ytterbium (Yb), yttrium (Y), or combination thereof.

4. The method of claim 2, wherein the precious metal ions comprise gold (Au), silver (Ag), platinum (Pt), palladium (Pd), rhodium (Rh), iridium (Ir) or combination thereof.

5. The method of claim 1, wherein the liquid containing the metal ions contacts with the extracellular protein at a temperature between 25°C. and 100°C.

6. The method of claim 1, wherein the liquid containing the metal ions contacts with the extracellular protein at a pH between 2 and 6.

7. The method of claim 1, wherein the liquid containing the metal ions comprises geothermal waters, boiler solutions, industrial wastewater or hard water.

8. A method for recycling metals in the treatment of boiler equipment, water pipelines, geothermal wells, industrial wastewater or hard water, comprising:
   culturing an isolated thermophilic bacterial strain in a culture medium;
   separating the thermophilic bacterial strain from the culture medium, wherein the culture medium comprises a mixture of extracellular proteins excreted by the thermophilic bacterial strain;
   concentrating the culture medium to a concentration of 50 ppm extracellular proteins, thereby obtaining a concentrated culture medium;
   contacting a volume of the concentrated culture medium with an equal volume of a liquid comprising metal ions, thereby forming a complex of the metal ions and the extracellular proteins, wherein the metal ions are from a metal to be recycled;
   collecting the complex of the metal ions and the extracellular proteins;
   adding a desorption agent to the complex of the metal ions and the extracellular proteins;
   wherein the isolated thermophilic bacterial strain is *Tepindimonas fonticaldi* sp. nov., internationally deposited in the Korean Collection of Type Culture (KCTC) with deposit number of KCTC 12528BP, wherein the desorption agent is selected from the group consisting of nitrilotriaceic acid, ethylenediaminetetraacetate, and a combination thereof.

* * * * *